ized *Bacillus* strain LSSAO1 is provided. When fed to

(12) United States Patent
Baltzley et al.

(10) Patent No.: US 8,455,238 B2
(45) Date of Patent: *Jun. 4, 2013

(54) MICROORGANISMS AND METHODS FOR TREATING POULTRY

(75) Inventors: Tammy Baltzley, Milwaukee, WI (US); Firmin Lago, Milwaukee, WI (US); Tony Neumann, Wauwatosa, WI (US); Thomas Rehberger, Wauwatosa, WI (US); Shelly Gebert, Hartford, WI (US)

(73) Assignee: DuPont Nutrition Biosciences ApS, Copenhagen (DK)

( * ) Notice: Subject to any disclaimer, the term of this patent is extended or adjusted under 35 U.S.C. 154(b) by 100 days.

This patent is subject to a terminal disclaimer.

(21) Appl. No.: 12/829,013

(22) Filed: Jul. 1, 2010

(65) Prior Publication Data
US 2010/0284981 A1 Nov. 11, 2010

Related U.S. Application Data

(63) Continuation of application No. 11/565,474, filed on Nov. 30, 2006, now Pat. No. 7,754,469.

(60) Provisional application No. 60/740,709, filed on Nov. 30, 2005.

(51) Int. Cl.
 *C12N 1/20* (2006.01)
(52) U.S. Cl.
 USPC ............... 435/252.5; 424/93.46; 424/93.462

(58) Field of Classification Search
None
See application file for complete search history.

(56) References Cited

U.S. PATENT DOCUMENTS 7,247,299 B2 * 7/2007 Lin et al. .................. 424/93.46
2005/0255092 A1 * 11/2005 Rehberger et al. ......... 424/93.46

OTHER PUBLICATIONS

Fritts et al., JAPR, 2000, vol. 9, p. 149-155.*
Teo et al., Applied & Environmental Microbiology, Aug. 2005, vol. 71, No. 8, p. 4185-4190.*
Barbosa et al., Applied and Environmental Microbiology, Feb. 2005, vol. 71, No. 2, p. 968-978.*

* cited by examiner

*Primary Examiner* — Kade Ariani
(74) *Attorney, Agent, or Firm* — Whyte Hirschboeck Dudek S.C.; Michael J. Cronin (57) ABSTRACT

An isolated *Bacillus* strain LSSAO1 is provided. When fed to a bird, this and other *Bacillus* strains described herein provide benefits to the birds. For example, administration of the one or more *Bacillus* strain can increase low G+C, gram positive bacteria in the gastrointestinal flora of the bird. These type of bacteria are increased by antibiotics and include beneficial *Clostridium*. Administration of the one or more *Bacillus* strain can also inhibit pathogen in the bird, such as *E. coli*, *Salmonella*, and *Clostridium*. These benefits can enhance feed conversion in poultry. Useful combinations of *Bacillus* strains and methods of using one or more *Bacillus* strain are also provided.

21 Claims, 5 Drawing Sheets

Figure 1. BioNumerics output file showing presence/absence of bands in jejunal sections on DGGE gels.

Figure 2. BioNumerics output file showing presence/absence of bands in Illeal sections on DGGE gels.

FIGURE 3

| | | |
|---|---|---|
| BB28-7 | ------------------------------------------------------------ | |
| BB28-16 | ------------------------------------------------------------ | |
| BB28-6 | ------------------------------------------------------------ | |
| X73447 | ACATCCTTCTGAC-TCTCCTTAATCGGAGATTCC-TTCGGGGACAGAAGTGACAGGTGG | 1007 |
| M59107 | ACATCCTTTGACCTCCTCCCTAATCGGAGATTTCCCTTCGGGGACAAGTGACAGGTGG | 1019 |

| | | |
|---|---|---|
| BB28-7 | TGCATGGTTGTCGTCAGCTCGTCGTCGTCAGCTGTTGGGTTAAGTCCCGCAACGAGCGCAA | 84 |
| BB28-16 | TGCATGGTTGTCGTCAGCTCGTCGTCGTCAGCTGTTGGGTTAAGTCCCGCAACGAGCGCAA | 70 |
| BB28-6 | TGCATGGTTGTCGTCAGCTCGTCGTCGTCAGCTGTTGGGTTAAGTCCCGCAACGAGCGCAA | 66 |
| X73447 | TGCATGGTTGTCGTCAGCTCGTCGTGATGTTGGGTTAAGTCCCGCAACGAGCGCAA | 1067 |
| M59107 | TGCATGGTTGTCGTCAGCTCGTCGTCGTGATGTTGGGTTAAGTCCCGCAACGAGCGCAA | 1079 |

| | | |
|---|---|---|
| BB28-7 | CCCTTATCTTCAGTAGCCAGCAATTCGGTTGGGCACTCTGACAGACTGCCAGGCAGAAC | 144 |
| BB28-16 | CCCTTATCTTCAGTAGCCAGCAGCGNTTCGGGCCGGCACTCTGAGAGACTGCCAGGGATAAC | 130 |
| BB28-6 | CCCNTATCTTTAGTAGCCAGCATTTAAGGTTGGGCACTCTAGAGAGACTGCCAGGGATAAC | 126 |
| X73447 | CCCTTGCCTTTAGTTGCCAGCA-TTAAGTTGGGCACTCTAGAGGGACTGCCAGG--TAAC | 1125 |
| M59107 | CCCTTGCCTTTAGTTGCCAGCA-TTAAGTTGGGCACTCTAGAGGGACTGCCAGNGATAAC | 1138 |

| | | |
|---|---|---|
| BB28-7 | CTGGAGGAAGGTGGGGATGACGTCAAATCATCATCCCCTTATGGCCAGGGCTACACACG | 204 |
| BB28-16 | CTGGAGGAAGGTGGGGATGACGTCAAATCATCATCCCCTTATGGCCAGGGCTACACACG | 190 |
| BB28-6 | TTGGAGGAAGGTGGGGATGACGTCAAATCATCATCCCCTTATGACCAGGGCTACACACG | 186 |
| X73447 | CTGGAGGAAGGTGGGGATGACGTCAAATCATCATCATCCCCTTATGCTTAGGGCTACACACG | 1185 |
| M59107 | CTGGAGGAAGGTGGGGATGACGTCAAATCATCATCATCCCCTTATGCTTAGGGCTACACACG | 1198 |

| | | |
|---|---|---|
| BB28-7 | TGCTACAATGGCGTAAACAAAGGGAGGCGAGCATGTGAGTGTGAGCAAATCTCAAAAATA | 264 |
| BB28-16 | TGCTACAATGGCGTAAACAAAGGGAGGCANAGCCGGAGCCGAGCCGAGCAAATCTCAAAAATA | 250 |
| BB28-6 | TGCTACAATGGCGTAAACAAAGGGAGGCANACCGGAGGTGGAGCCGAGCAAATCCAAAAATA | 246 |
| X73447 | TGCTACAATGGTGGTACAGAGGGCAGCCAAGTCGTGAGGCCGAGCTAATCCCTTAAAGC | 1245 |
| M59107 | TGCTACAATGGTGGTACAGAGGGCAGCCAAGTCGTGAGGCCGAGCTAATCCCTTAAAGC | 1258 |

| | | |
|---|---|---|
| BB28-7 | ACGTCTCAGTTCGGATTGTAGTCTGCAACTCGACTACATGAAGCTGGAATCGCTAGTAAT | 324 |
| BB28-16 | ACGTCTCAGTTCGGATTGTAGTCTGCAACTCGACTACATGAAGCTGGAATCGCTAGTAAT | 310 |
| BB28-6 | ACGTCTCAGTTCGGATTGTAGTCTGCAACTCGACTACATGAAGCTGGAATCGCTAGTAAT | 306 |
| X73447 | CATTCTCAGTTCGGATTGTAGGCTGAAACTCGCCTACATGAAGCTGGAGTTACTAGTAAT | 1305 |
| M59107 | CATTCTCAGTTCGGATTGTAGGCTGAAACTCGCCTACATGAAGCTGGAGTTACTAGTAAT | 1318 |

| | | |
|---|---|---|
| BB28-7 | CGGGATCAGCATGCCGCGGTGAATACGTTCCCGGGTCTTGTACACACCG--------- | 374 | SEQ ID NO:6 |
| BB28-16 | CCGGAATCAGAATGTCGCGGTGAATACGTTCCCGGGTCTTGTACACACCGA-------- | 361 | SEQ ID NO:7 |
| BB28-6 | CCGGAATCAGAATGTCGCGGTGAATACGTTCCCGGGTCTTGTACACACCGA-------- | 357 | SEQ ID NO:8 |
| X73447 | CGCAGATCAGAATGCTGCGGTGAATGCGTTCCCGGGTCTTGTACACACCGCCCGTCACAC | 1365 | SEQ ID NO:9 |
| M59107 | CGCAGATCAGAATGCTGCGGTGAATGCGTTCCCGGGTCTTGTACACACCGCCCGTCACAC | 1378 | SEQ ID NO:10 |

Figure 4: Average APEC Counts: Control Vs. Treated

Figure 5: Cumulative % Mortality of Treated versus Paired Control Flocks

Figure 6. Feeding trial phase 1, percent of confirmed *Salmonella*.

Figure 7. Feeding trial phase 2, percent of confirmed *Salmonella*.

MICROORGANISMS AND METHODS FOR TREATING POULTRY

CROSS-REFERENCE TO RELATED APPLICATIONS

This application is a continuation application of U.S. Utility patent application Ser. No. 11/565,474, filed on Nov. 30, 2006, which claims priority under 35 U.S.C. §119(e) to U.S. Provisional Patent Application No. 60/740,709, filed Nov. 30, 2005, the entirety of which is incorporated by reference herein.

FIELD OF THE INVENTION

This invention relates to compositions of novel microorganisms for treating and preventing poultry diseases and enhancing feed conversion in poultry.

SUBMISSION OF SEQUENCE LISTING

The contents of the electronic submission text file sequence listing is incorporated herein by reference in its entirety.

BACKGROUND OF THE INVENTION

Several infections and diseases in poultry are caused by pathogenic bacteria, including *E. coli, Clostridium*, and *Salmonella*. Infections and diseases caused by pathogens result in increased mortality, decreased performance, and increased cost of turkey production. In addition, many of these pathogens can be transmitted to humans.

Avian colibacillosis is a systemic infection caused by *E. coli* and occurs most commonly in young broilers and poults. Avian pathogenic *E. coli* (APEC) comprise a specific subset of pathogenic *E. coli* that cause extraintestinal diseases of poultry. (Snoeyenbos, G. H., et al. 1977 Avain Diseases. 22:273-287.) APEC consists mainly of enteropathogenic *E. coli* (EPEC) and enterotoxigenic *E. coli* (ETEC) serovars, i.e., subdivisions of a species or subspecies distinguishable from other strains therein on the basis of antigenicity. (Wiard, T., et al. 2003. Poult. Sci. Asso. Supplement 1:58-59.) APEC is found in the intestinal microflora of healthy birds and infections are enhanced or initiated by secondary environmental and host predisposing factors. Colibacillosis is a common systemic infection caused by APEC, and occurs most commonly as acute septicemia or subacute aerosacculitis and polyserositis in chickens, turkeys, and other avian species (Zhu, X. Y., et al. 2002. Appl. Environ. Microbiol. 68:124-137.).

*Clostridium* affecting poultry include *C. perfringens, C. septicum*, and *C. botulinum* which are anaerobic, gram-positive, spore-forming rods that produce potent toxins. Gangrenous dermatitis and cellulitis have reemerged recently as a significant concern for poultry producers in the U.S. Characterized by necrosis of the skin, subcutaneous tissue, and often the underlying musculature, the disease occurs suddenly and progresses rapidly with death occurring often before the first symptoms are observed. Crepitus tissue caused by gas accumulation under the affected skin is also commonly observed in cases of GD and cellulitis. The anaerobic, spore-forming, gram-positive rod *Clostridium* has been implicated in numerous cases of necrotizing soft-tissue infections in poultry (Carr, D., et al. 1996. Avian Dis 40:736-41; Hofacre, C. L., et al. 1986. Avain Dis 30:620-2; Willoughby, D. H., et al. 1996. J Vet Diagn Invest 8:259-61). The two most commonly isolated species have been *C. perfringens* and *C. septicum*. *C. perfringens* is ubiquitous in nature, commonly found in the soil and gastrointestinal tracts of warm blooded animals. It produces α-toxin and θ-toxin that work synergistically to produce the pathology observed in *C. perfringens* associated clostridial myonecrosis (Awad, M. M., et al. 2001. Infect Immun 69:7904-10.). *C. septicum* is a very virulent, but poorly understood pathogen that is recognized as the causative agent of atraumatic myonecrosis. It also produces α-toxin, distinct from *C. perfringens*, which acts as a pore-forming cytolysin and is essential for virulence (Kennedy, C. L., et al. 2005. Mol Microbiol 57:1357-66.). In order to better understand the etiology of this disease and the diversity of the *Clostridium* implicated, microbiological analysis of affected birds' organs and tissues was performed. The results suggest a clostridial bacteremia present prior to death with both species and multiple strains involved.

The spores of *C. botulinum* are heat-resistant and can survive in foods that are incorrectly or minimally processed. Food borne botulism (as distinct from wound botulism and infant botulism) is a severe type of food poisoning caused by the ingestion of foods containing the potent neurotoxin formed during growth of the organism. The toxin is heat labile and can be destroyed if heated at 80° C. for 10 minutes or longer. The incidence of the disease is low, but the disease is of considerable concern because of its high mortality rate if not treated immediately and properly. Most of the 10 to 30 outbreaks that are reported annually in the United States are associated with inadequately processed, home-canned foods, but occasionally commercially produced foods have been involved in outbreaks.

Strains of *Salmonella* cause Salmonellosis, which occurs in animals, including humans. It is an enteric disease of varying severity, usually involving diarrhea. With poultry, however, most *Salmonella* infections are symptomless. Many strains of *Salmonella* are zoonotic agents, spreading to humans from contaminated food products. In humans, Salmonellosis is one of the most common causes of food poisoning.

Thus, pathogenic bacteria are a major problem for poultry producers. Further complicating this situation is the fact that pathogen populations in poultry production facilities typically fluctuate in terms of both levels and types of pathogens, making control of the pathogens difficult. An adequate disease prevention program is essential to a profitable commercial poultry operation. Chronic diseases can reduce efficiency and increase costs.

To prevent disease in and stimulate growth of turkeys, antibiotics have been used. Fed at a sub-therapeutic level, antibiotics have been found to have beneficial effects. For example, antibiotics reduce levels of lactic acid bacteria, which in adult animals are not needed and can be problematic. In addition, antibiotics increase low G+C, gram positive bacteria, including beneficial *Clostridium*. See, e.g, WO 2004/104175 to Lee, M. D. et al.

However, there are many drawbacks associated with antibiotic use, such as consumer acceptance and selection of resistant bacteria. For instance, mounting scientific evidence shows that using antibiotics in livestock feed can lead to antibiotic-resistant bacteria that can be transferred to people, making it harder to treat certain infections.

Concerns over antibiotics have led the European Union on Jan. 1, 2006 to ban the feeding of all antibiotics and related drugs to livestock for growth promotion purposes. The sweeping new policy follows up a 1998 ban on the feeding of antibiotics that are valuable in human medicine to livestock for growth promotion. Now, no antibiotics can be used in European livestock for growth promotion purposes.

In the United States, a bill banning low-level feeding of seven antimicrobials (bacitracin, erythromycin, lincomycin, penicillin, tetracycline, tylosin, and virginiamycin) was introduced into the House of Representatives in November 1999 (H.R. 3266).

Accordingly, there is a recognized need for alternatives, such as microorganisms and methods of using microorganism for treating or preventing disease in poultry. Furthermore, there is an important need for improving performance in and health of poultry.

SUMMARY OF THE INVENTION

The invention, which is defined by the claims set out at the end of this disclosure, is intended to solve at least some of the problems noted above. An isolated *Bacillus* strain LSSAO1 is provided. When fed to a bird, this and other *Bacillus* strains described herein provide benefits to the birds. For example, administration of the one or more *Bacillus* strain can increase low G+C, gram positive bacteria in the gastrointestinal flora of the bird. These type of bacteria are increased by antibiotics and include beneficial *Clostridium*. Administration of the one or more *Bacillus* strain can also inhibit pathogen in the bird, such as *E. coli, Salmonella,* and *Clostridium*. These benefits can enhance feed conversion in poultry.

Also provided is a combination comprising two or more isolated *Bacillus* strains chosen from at least one of strains LSSAO1, 3A-P4, 15A-P4, 22C-P1, BS27, and 2084.

In addition, a method of using one or more of the *Bacillus* strains provided herein is provided. In the method, an effective amount of at least one isolated *Bacillus* strain is administered to one or more bird. The administration of the strain providing at least one of the following benefits: an increasing low G+C, gram positive bacteria in the gastrointestinal flora of the bird and an inhibition of a pathogen, such as *E. coli, Salmonella,* and *Clostridium* in the bird.

BRIEF DESCRIPTION OF THE DRAWINGS

Preferred exemplary embodiments of the invention are illustrated in the accompanying drawings, in which like reference numerals represent like parts throughout and in which:

FIG. 3 is a sequence alignment of DNA sequences for the 16S rDNA of the BB28-7, BB28-16, and BB28-6 ribotypes, which represent samples obtained from DGGE gels from turkeys treated with a *Bacillus* CSI product of the invention and two *Clostridia* spp. (NCBI Accession # X73447 and M59107) known to be promoted by the growth promoting antibiotic virginiamycin. These sequences were aligned using ClustalW.

DETAILED DESCRIPTION

Definitions

The following definitions are intended to assist in providing a clear and consistent understanding of the scope and detail of the terms:

As used herein, "active metabolite" means a substance produced by bacteria and that has antibacterial activity towards other bacteria.

As used herein "basemix" or "concentrated basemix" refers to *Bacillus* strains added to a carrier to make a basemix form. The concentrated form is composed of the *Bacillus* strains added the carrier in a more concentrated form. The basemix or concentrated basemix forms are then be added to the feed at a desired inclusion rate and fed to the animal.

As used herein, "performance" refers to the growth of an animal, such as a bird, measured by the following parameters: average daily weight gain, total weight gain, feed conversion, which includes both feed:gain and gain:feed, feed efficiency, mortality, and feed intake.

"An improvement in performance" as used herein, means an improvement in at least one of the parameters listed above under the performance definition.

In accordance with the present invention there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Microorganisms for treating and preventing poultry diseases and improving performance in poultry are provided. In one embodiment of the invention, microorganisms are *Bacillus*. One or more *Bacillus* strains can be used. The *Bacillus* strain(s) can be fed to poultry as a direct-fed microbial. Feeding one or more *Bacillus* strains described herein to poultry reduces or prevents poultry diseases and improves performance and health in poultry.

*Bacillus* strains were selected based on their ability to inhibit pathogenic bacteria and/or to mimic the effects of antibiotics, such as virginiamycin.

*Bacillus* Strains

Characterization and Screening of *Bacillus* Strains:

*Bacillus* strains described herein were obtained from various environmental samples and a library of *Bacillus* strains. The *Bacillus* strains described herein were selected by identifying representative pathogens present in a poultry flock. Once pathogens were identified, *Bacillus* strains were screened to determine which of them inhibit growth of the identified pathogens. Aerobic and facultative spore-formers of the genus *Bacillus* were isolated.

Through necropsy sessions, pathogenic *E. coli, Salmonella,* and *Clostridium* isolates were identified from multiple birds. Colonies were then isolated. DNA was isolated from the colonies, and multiplex PCR was performed. Multiplex PCR was used to determine if the isolates are pathogenic.

Through the detection of virulence factors, the isolates were compared using RAPD-PCR. From the RAPD-PCR results, clusters of *E. coli, Salmonella*, and *Clostridium* were identified.

*Bacillus* strains were selected that inhibited representative members from the clusters of pathogenic bacteria. For this, plates were seeded, each with a specific pathogen from a flock. The seeded plates were overlaid with a *Bacillus* strain and incubated to determine if the *Bacillus* strain inhibited the pathogen that had been seeded in the plate. After incubation, the plates were observed for zones of inhibition for each pathogen. Colonies of *Bacillus* that produced a zone of inhibition were then picked. The isolates were grown.

*Bacillus* strains have many qualities that make them useful for compositions that are ingested by animals. For example, *Bacillus* strains produce extracellular enzymes, such as proteases, amylases, and cellulase. In addition, *Bacillus* strains produce antimicrobial factors, such as gramicidin, subtilin, bacitracin, and polymyxin. Furthermore, *Bacillus* strains are spore-formers and thus are stable. Additionally, several species of *Bacillus* have GRAS status, i.e., they are generally recognized as safe. *Bacillus* species are the only spore-formers that are considered GRAS.

The *Bacillus* strains described herein inhibit one or more strains of pathogenic bacteria, including *E. coli, Salmonella*, and *Clostridium*. Multiple *Bacillus* strains can be combined for control of various pathogens such as *E. coli, Salmonella*, and *Clostridium.*

Although not intended to be a limitation to the present disclosure, it is believed that inhibition of pathogens is accomplished via the secretion of an active metabolite from the *Bacillus*. While applicants do not wish to be restricted to a particular theory of how an active metabolite would inhibit microbial growth and do not intend to limit the present disclosure, it is believed that a proteinaceous and bacteriocidal or bacteriostatic active metabolite is secreted.

In addition to the direct inhibition of the pathogenic bacteria in the gastrointestinal tract and production environment, feeding *Bacillus* strains has also been shown to modulate the gastrointestinal microbial communities. The changes in the gastrointestinal communities associated with feeding *Bacillus* strains has been characterized using molecular DNA techniques including denaturing gradient gel electrophoresis. Feeding *Bacillus* to poultry has been shown to result in an increase in the gram-positive low G/C microorganisms. These low G/C gram-positive organisms are generally related to a number of species of non-pathogenic clostridial organisms. Identical results have been found when feeding the antibiotic virginiamycin and may explain the growth promoting effect of this antibiotic.

*Bacillus* strains identified as being useful against poultry pathogens and for mimicking effect of antibiotics, such as virginiamycin, include strains 3A-P4, 15A-P4, 22C-P1, BS27, 2084, and LSSA01. These strains can be fed individually or in combination with each other. Other *Bacillus* strains are also included within the scope of the invention.

On Jan. 12, 2005, strains 3A-P4, 15A-P4, and 22C-P1 were deposited at the American Type Culture Collection (ATCC), 10801 University Blvd., Manassas, Va. 20110-2209 and given accession numbers PTA-6506 (3A-P4), PTA-6507 (15A-P4), and PTA-6508 (22C-P1), respectively. Strains 2084, LSSAO1, and BS 27 were deposited on Mar. 8, 2007, Jan. 22, 2008, and Jan. 24, 2008, respectively, at the Agricultural Research Service Culture Collection (NRRL), 1815 North University Street, Peoria, Ill., 61604 and given accession numbers NRRL B-50013, NRRL B-50104, and NRRL B-50105, respectively. The deposits were made under the provisions of the Budapest Treaty on the International Recognition of the Deposit of Microorganisms for the Purposes of Patent Procedure.

*Bacillus* strains 3A-P4, 15A-P4, and 22C-P1 were isolated from different geographical regions of North America and from different environmental sources. Specifically, strain 3A-P4 was isolated from chicken litter from Canada, strain 15A-P4 was isolated from turkey litter from the Western United States, and strain 22C-P1 was isolated from a swine lagoon from the Eastern United States.

For all the *Bacillus* strains, growth times were determined for production of an optimal level of the active metabolite using the broth activity method. For this, active metabolite was added to a culture of *Clostridia* or *E. coli* and optical densities (ODs) were read at various time points.

*Bacillus* Strains as Direct-Fed Microbials:

*Bacillus* strains of the invention can enhance performance in poultry. Therefore, it is economical for a producer to routinely include one or more *Bacillus* strain, either individually or in combination with other *Bacillus* strains, in feed not only to treat and prevent disease but also to improve performance.

*Bacillus* strains can be directly fed to poultry also to inhibit pathogenic poultry disease. Feeding microorganisms that have GRAS status, such as *Bacillus* strains of the invention, to livestock is an acceptable practice amongst producers, veterinarians, and others in the livestock industry. By inhibiting pathogens in poultry, the *Bacillus* strain(s) reduces and even prevents disease in poultry.

*Bacillus* strains can be administered as a preventative to poultry not currently infected with pathogens. In one embodiment, one-day-old poults or chicks are fed one or more *Bacillus* isolates throughout brood phase to inhibit or even prevent outbreaks of disease and to improve performance. One or more *Bacillus* isolate can also be fed at other phases also. Routine administration of the microorganisms can dramatically reduce and even eliminate outbreaks of disease at animal production facilities and enhance performance.

Preparation and Feeding *Bacillus* Direct-Fed Microbials:

*Bacillus* strains of the invention can be administered as a direct-fed microbial. Administration of one or more microorganisms to animals is accomplished by any convenient method, including adding the *Bacillus* strains to the animals' drinking water, to their feed, or to the bedding or litter, or by direct oral insertion, such as by an aerosol. *Bacillus* strains preferably are administered as spores.

*Bacillus* strains may be presented in various forms, for example as a top dress, liquid drench, gelatin capsule, or gels. In one embodiment of the top dress form of the strain, freeze-dried *Bacillus* fermentation product is added to a carrier, such as whey, maltodextrin, sucrose, dextrose, limestone (calcium carbonate), rice hulls, yeast culture, dried starch, sodium silico aluminate. In one embodiment of the liquid drench, freeze-dried *Bacillus* fermentation product is added to a carrier, such as whey, maltodextrin, sucrose, dextrose, dried starch, sodium silico aluminate, and a liquid is added to form the drench. In one embodiment of the gelatin capsule form, freeze-dried *Bacillus* fermentation product is added to a carrier, such as whey, maltodextrin, sugar, limestone (calcium carbonate), rice hulls, yeast culture dried starch, and/or sodium silico aluminate. The *Bacillus* and carrier are enclosed in a degradable gelatin capsule. In one embodiment of the gels form, freeze-dried *Bacillus* fermentation product is added to a carrier, such as vegetable oil, sucrose, silicon dioxide, polysorbate 80, propylene glycol, butylated hydroxyanisole, citric acid, and artificial coloring to form the gel.

The *Bacillus* strains are grown in a liquid nutrient broth, preferably to a level at which the highest number of spores are formed. In a preferred embodiment, the strains are grown to an OD where the spore yield is at least $1\times10^9$ colony forming units (CFU) per ml of culture. The *Bacillus* strains of the present invention are produced by fermentation of the bacterial strains. Fermentation is started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is Trypticase Soy Broth. After the inoculum is added to the fermentation vessel, the temperature and agitation are controlled to allow maximum growth. Once the culture reaches a maximum population density, the culture is harvested by separating the cells from the fermentation medium. This is commonly done by centrifugation. The count of the culture can then be determined.

The count of the bacteria is important when combined with a carrier. At the time of manufacture of the composition, the *Bacillus* count preferably is at least about $1.0\times10^{11}$CFU/g. The counts may be increased or decreased from these base numbers and still have complete efficacy. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

To prepare compositions, the cultures and the carrier can be added to a ribbon or paddle mixer and mixed preferably for about 15 minutes. The components are blended such that a uniform mixture of the carrier and cultures result. The final product is preferably a dry flowable powder.

The preferred dosage range of the liquid drench and gel is about $1\times10^4$ CFU/g or ml/day to about $1\times10^{10}$ CFU/g or ml/day, and more preferably about $1\times10^6$ CFU/g or ml/day. The preferred dosage range of the top dress, basemix, and premix is about $1\times10^3$ CFU/g of feed to about $1\times10^8$CFU/g of feed, and more preferably about $1\times10^5$CFU/g of feed. The preferred dosage range for inclusion into water is about $1\times10^3$ CFU/animal/day to about $1\times10^{10}$ CFU/animal/day, and more preferably about $1\times10^7$ CFU/animal/day. While these examples use freeze-dried *Bacillus* as an ingredient in the top dress, liquid drench, gels, water, and feed forms, it is not necessary to freeze-dry the *Bacillus* before feeding it to animals. For example, spray-dried, fluidized bed dried, or solid state fermentation *Bacillus* or *Bacillus* in other states may be used. The microorganisms can also be administered in a wet cell slurry paste, with or without preservatives, in concentrated, unconcentrated, or diluted form.

In one embodiment, one or more of the following *Bacillus* strain are used with the strain having a count of $1\times10^5$ CFU/g: strain 3A-P4, 15A-P4, 22C-P1, strain BS 27, strain 2084, and strain LSSA01. The *Bacillus* strains can be combined in different ratios to determine the best ratio to inhibit poultry pathogens and improve performance. When used in combination, the following exemplary, non-limiting ratios of *Bacillus* strains can be used: 1/3 each of three different strains; 1/4 each of four different strains; 40% of a first strain, 40% of a second strain, and 20% of a third strain. Other combinations of strains can also be used. In addition, a combination having 50% more CFU per gram can be used to boost the amount of microorganism fed to the animal. A final bacteria count of about $1\times10^5$ CFU/g to about $1\times10^6$ CFU/g can be used. In one embodiment, about $7.5\times10^4$ CFU/g is used.

In one embodiment, *Bacillus subtilis* strains BS 27, 2084, and 22CP1 are used. These *B. subtilis* strains can be supplied in a dry granular form, a liquid concentrate form, or other forms. An exemplary count of the strains in the dry granular form is $1.18\times10^9$ CFU/gram ($5.34\times10^9$ CFU/lb). The dry granular form can be supplied as freeze-dried spores in a free flowing carrier. An exemplary count of the strains in the liquid concentrate is $1.0\times10^9$ CFU/ml ($6.6\times10^{10}$ CFU/ton). The liquid concentrate can be supplied as stabilized spores in water. The *B. subtilis* strains BS 27, 2084, and 22CP1 are mixed at 33% of each strain and configured to apply $7.5\times10^4$ CFU/g of the strains in the final feed. In one embodiment, over 95% of the *B. subtilis* strains are in spore form. All *B. subtilis* strains are GRAS. All strains are heat resistant to 160° F. and can be pelleted in feed.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Design. Gastrointestinal samples from finishing phase turkeys within a production system were sampled to examine pathogen populations and microbial diversity.

Within the turkeys sampled were two treatments: an experimental group that was treated with a CSI-*Bacillus* DFM and a control, no treatment group. The *Bacillus* CSI consisted of strains 22CP1, 2084 and BS 27, with each strain consisting of one-third the total count of $7.5\times10^4$ CFU/g of feed. Three birds from each of four houses (2 treated, 2 control) were sampled. Bird ages for treated houses were 13 weeks and 6 weeks, and the controls birds were 18 weeks and 14 weeks.

Bird/intestinal collection. Turkey poults were sacrificed from each of the 25 sampling houses. The birds ranged in age from 23 to 32 days. Intestinal tracts were removed, tied off at the esophageal and cecal ends, and immediately placed in sterile whirl-pak bags with sterile saline covering the entire tract. Tract samples were shipped overnight to Agtech Products for further testing. Upon arrival at Agtech, each section of the gastrointestinal tract (D, J, and I) was treated as an individual sample.

DNA isolation, PCR, and DGGE. Total genomic DNA was isolated from two 500 μl aliquots of each sample using the Roche Applied Science High Pure PCR Template Preparation Kit per the manufacture's instructions (Mannheim, Germany). Genomic DNA was visualized on a 0.7% agarose gel stained with ethidium bromide (500 ng per liter ddH20). DNA template concentration was measured using a fluorometer with PicoGreen quantitation reagents from Molecular Probes, Inc. (Eugene, Oreg.). The V6-V8 region of the 16S rDNA corresponding to positions 968 to 1401 in *Escherichia coli* (Brosius, J., et al. 1981. Proc. Natl. Acad. Sci. USA 75:4801-4805) was amplified by polymerase chain reaction (PCR) using the Platinum Taq DNA polymerase from Invitrogen Life Technologies (Carlsbad, Calif.). PCR mixtures (50 μl) contained 75 ng genomic DNA, 2.5 units of Taq polymerase, 1×PCR Buffer, 2.0 mM MgCl2, 200 μM each deoxynucleoside triphosphate, 50 pmol of each primer (968f+G/C clamp 5'-CGCCCGCCGCGCCCCGCGCCCGTCCCGC- CGCCCCCGCCCGAACGCGAAGAAC CTTAC-3' (SEQ ID NO: 1) and 1401r 5'-CGGTGTGTACAAGACCC-3' (SEQ ID NO: 2)) (Zhu et al., 2002), and water. PCR was carried out on a MJ Research DNA Engine Opticon 2 thermocycler (Reno, Nev.). The PCR amplification program started with an initial denaturation at 95° C. for 5 min, followed by 30 cycles of incubations at 95° C. for 30 s, 59.5° C. for 45s, and 72° C. for 1 min, and completed with a final extension at 72° C. for 7 min. PCR products were confirmed by electrophoresis on a 1% agarose gel stained with ethidium bromide as previously described.

With a BioRad Dcode Universal Mutation Detection System (Hercules, Calif.) the PCR products were separated by DGGE according to Muyzer et al. with the following modifications. Electrophoresis was performed on a 5% polyacrylamide gel (37.5:1 acrylamide-bisacrylamide; dimensions 16 cm by 16 cm by 1 cm) using a 15 to 45% linear denaturing gradient (100% denaturing solution contained 40% (vol/vol) formamide and 7 M urea). Gels were electrophoresed for 4 h at 130 V in 0.5×TAE buffer at a constant temperature of 60° C. Each gel was then stained for 10 min in ethidium bromide (250 ng per 500 ml 0.5×TAE) and destained for 10 min in 0.5×TAE. Digital photographs were taken using the Syngene BioImaging system (Cambridge, UK).

Analysis. DGGE images were analyzed using Applied Maths BioNumerics software package (Austin, Tex.). Ribotype (band) counts were compared across treatments.

MANOVA discriminative analysis was used to compare the four treatment groups and three ages to identify possible targets.

Target Identification. Ribotypes identified by discriminative analysis as important in relation to treatment were excised from the gel. The band was purified using QIAGEN's QIAEXII kit (Valencia, Calif.) according to manufacture's protocol. DNA quantity was increased by nested-PCR(N-PCR) with similar PCR conditions as stated previously, substituting the forward primer with 968f 5'-AACGCGAA-GAACCTTAC-3'(SEQ ID NO: 3). Each N-PCR sample was purified before visualization using QIAGEN's PCR Purification Kit (Valencia, Calif.). Samples were then sent to Lark Technologies (Houston, Tex.) for sequencing. Resulting sequences were compared to the NCBI database with a Blast search for preliminary identification.

Target Strains Identification. The targets were identified using the BioLog microbial identification system (Hayward, Calif.) according to manufactures protocol. Each of the targets was also identified using 16S rDNA sequencing. Briefly, primers corresponding to the region from 8 to 1406 of the 16S rDNA of *Escherichia coli* were amplified using the Platinum Taq DNA polymerase from Invitrogen Life Technologies (Carlsbad, Calif.). PCR mixtures contained 2 µl of genomic DNA, 2.5 units of Taq polymerase, 1×PCR Buffer, 1.5 mM MgCl2, 200 µM each deoxynucleoside triphosphate, 10 pmol of each primer (8f 5'-AGAGTTTGATYMTGGCTCAG-3' (SEQ ID NO: 4) and 1406r 5'-ACGGGCGGTGTGTRC-3' (SEQ ID NO: 5)), and water to a final volume of 50 µl. The PCR amplification program started with an initial denaturation at 95° C. for 5 min, followed by 32 cycles of incubations at 94° C. for 30s, 57.5° C. for 45 s, and 72° C. for 2 min, and completed with a final extension at 72° C. for 7 min on an ABI 2720 thermocycler. PCR products were confirmed by electrophoresis on a 1% agarose gel stained with ethidium bromide as previously described. PCR products were then handled as previously mentioned.

Figure 1:
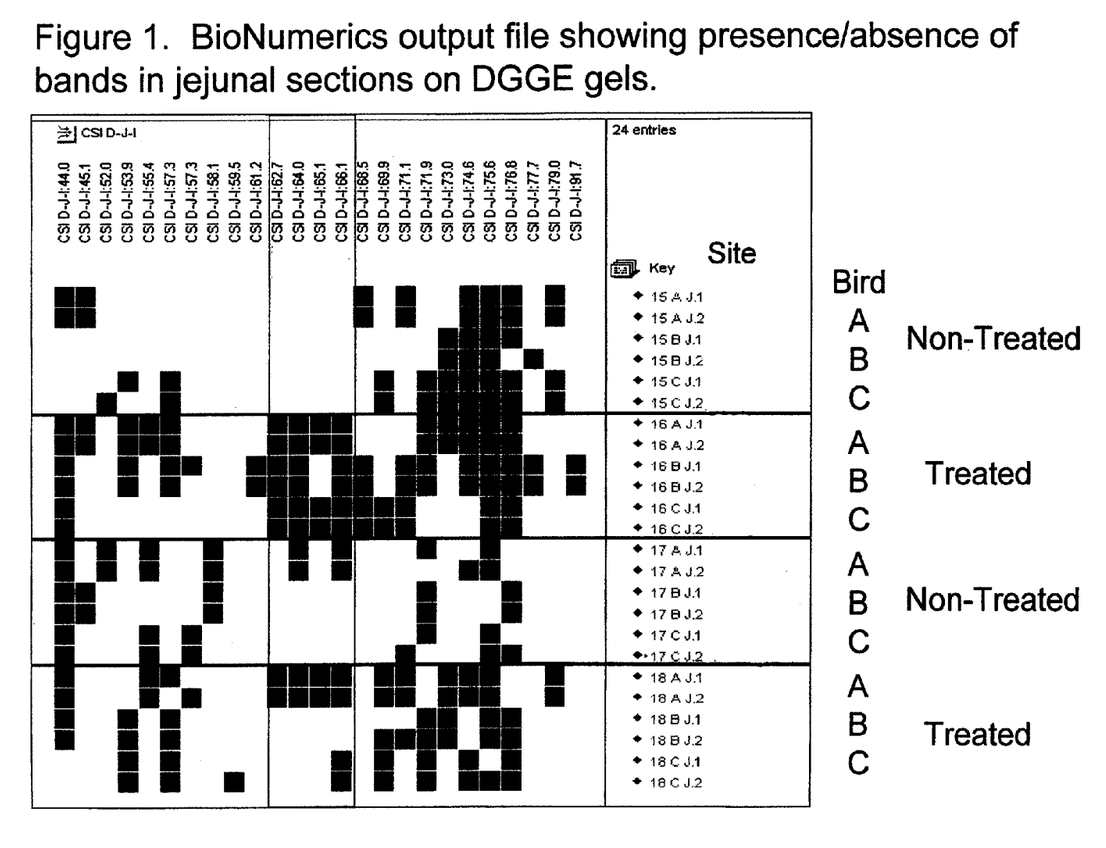
FIG. 1 shows a BioNumerics™ output file showing the presence or absence of bands in jejunal sections on denaturing gradient gel electrophoresis (DGGE) gels.
Figure 2:
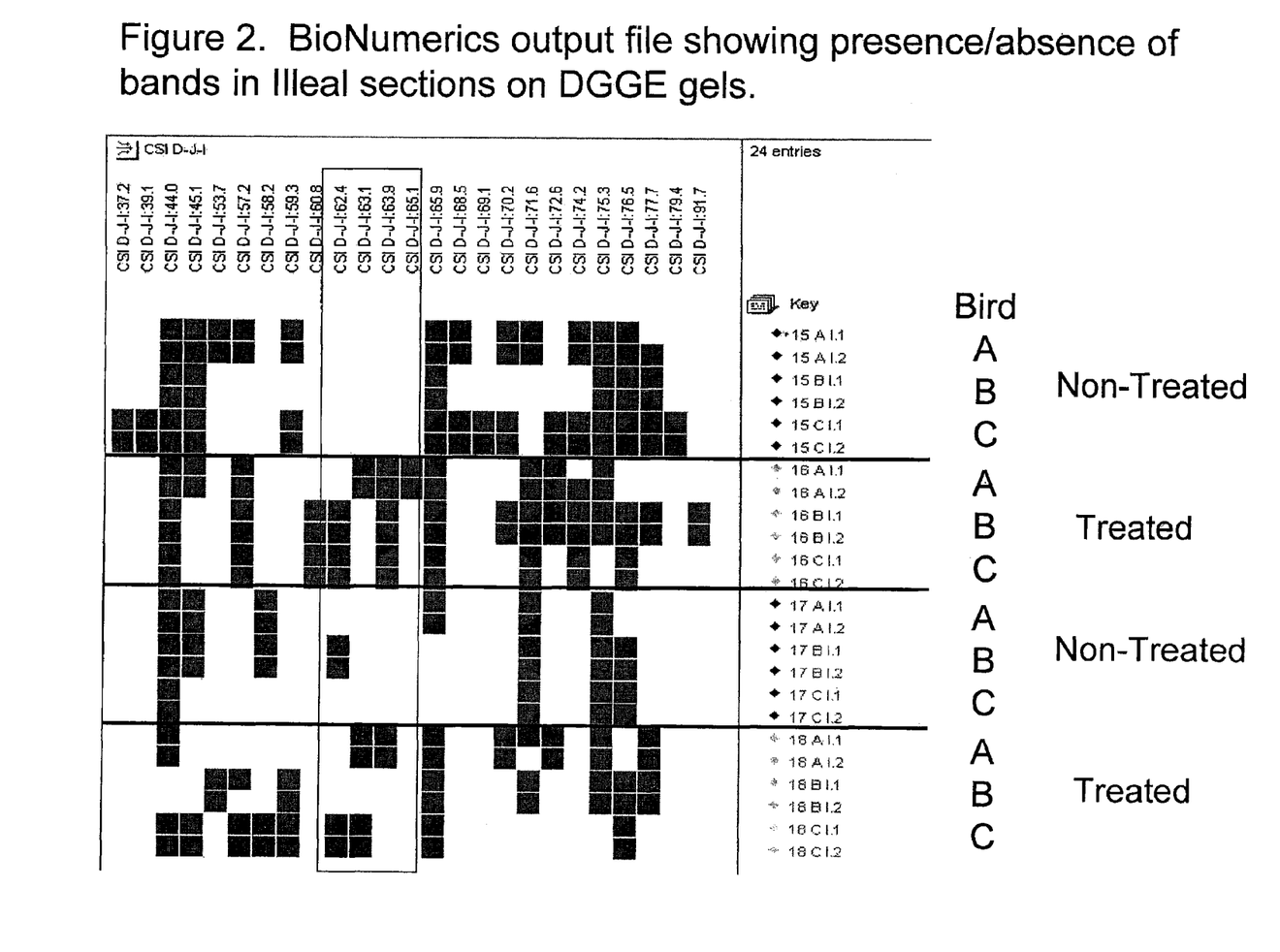
FIG. 2 shows a BioNumerics™ output file showing the presence or absence of bands in illeal sections on denaturing gradient gel electrophoresis (DGGE) gels.

The resulting DGGE images were analyzed using the BioNumerics software using discriminative characters. The analysis shows presence or absence of ribotypes (bands) across all selected samples. Interestingly, the results revealed a group of ribotypes that were more often present in the CSI-*Bacillus* DFM treated birds then the controls. (Highlighted with the boxes on FIGS. 1 and 2). This group of ribotypes was discovered in both the jejunal (FIG. 1) and illeal (FIG. 2) portions of the tract.

DNA sequences for the 16S rDNA of the BB28-7, BB28-16, and BB28-6 ribotypes, which represent samples obtained from DGGE gels from turkeys treated with the CSI-*Bacillus* DFM, were obtained as is described above. Referring now to FIG. 3, these sequences were aligned using ClustalW, and were also aligned with two *Clostridia* spp. (NCBI Accession # X73447 and M59107) known to be promoted by the growth promoting antibiotic virginiamycin. See WO 2004/104175 to Lee, M. D. et al. These *Clostridia* spp. are beneficial bacteria. Asterisks in the alignment denote identical sequences. The bacteria that are associated with the CSI-*Bacillus* DFM treatment have a high amount of homology to these *Clostridia* spp. Therefore, evidence is provided that feeding a CSI-*Bacillus* DFM to finishing turkeys naturally alters their gastrointestinal microflora similar to the growth promoting antibiotic Virginiamycin.

In summary, feeding the CSI-*Bacillus* DFM to finishing turkeys naturally alters their gastrointestinal flora similar to the growth promoting antibiotic virginiamycin.

Example 2

Utilization of Strain 2084 in the Diets of Male Broiler Chickens

Introduction. A battery trial was conducted to determine the effects of strain 2084, a *Bacillus* based direct-fed microbial feed additive, on the performance of male broilers grown to 28 days of age.

Materials and Methods. A starter and grower basal diet utilizing corn and soybean meal as the primary ingredients were formulated to contain 105% of the 1994 National Research Councils recommended nutrient requirement for male broilers. Diet compositions and analyzed nutrient content are shown in Tables 1 and 2. The test ingredient was then added to each of these diets and blended with BMD-50 at either 0 or 50 grams/ton drug activity. The levels of *Bacillus* delivered per gram of feed for the 0.25% and 0.5% inclusion rates were $3.75 \times 10^4$ and $7.5 \times 10^4$ colony forming units. Dietary treatments were arranged in a 3×2 factorial to give a total of 6 treatments. All diets were mixed for approximately five minutes and then pelleted at 175° F. The starter diet was also crumbled. Each diet was fed to ten replications of six male broilers of a commercial high yield strain (Cobb 500× Cobb 500). The starter diets were fed from day one to day fourteen and the grower diets were fed from day fourteen to day twenty-eight. At the end of the starter period, the remaining starter feed was removed and weighed before the grower feed was added to each pen.

TABLE 1

Diet Composition

| Ingredient | Starter Diets g/kg | Grower Diets g/kg |
|---|---|---|
| Yellow Corn | 583.39 | 627.45 |
| Soybean Meal | 312.58 | 285.49 |
| Poultry Oil | 39.85 | 45.79 |
| Corn Gluten Meal | 13.27 | 0.0 |
| Dicalcium Phosphate | 17.04 | 15.05 |

TABLE 1-continued

Diet Composition

| Ingredient | Starter Diets g/kg | Grower Diets g/kg |
|---|---|---|
| Limestone | 13.06 | 12.15 |
| Salt | 4.36 | 4.45 |
| Vitamon Premix | 5.00 | 5.00 |
| Trace Mineral Premix | 1.00 | 1.00 |
| DL Methionine | 2.44 | 2.20 |
| Lysine HCl | 1.53 | 0.0 |
| BMD-50[1] | 0.50 | 0.50 |
| Total | 1000.0 | 1000.0 |

[1]In diets that do not contain BMD-50, corn was used to replace the amount of BMD-50 removed from the diet.

TABLE 2

Analyzed Nutrient Content of the Test Diets

| Diet (BMD, strain 2084) | Crude Protein (%) | Dry Matter (%) | Ash (%) | Crude Fat (%) |
|---|---|---|---|---|
| Starter 0, 0 | 23.2 | 88.5 | 4.9 | 5.6 |
| Starter 0, .25 | 24.0 | 88.5 | 5.2 | 5.8 |
| Starter 0, .50 | 23.6 | 88.1 | 5.0 | 5.6 |
| Starter 50, 0 | — | — | — | — |
| Starter 50, .25 | 24.3 | 87.9 | 5.0 | 6.0 |
| Starter 50, .5 | 23.6 | 88.3 | 5.0 | 5.5 |
| Grower 0, 0 | 21.3 | 87.9 | 5.2 | 6.8 |
| Grower 0, .25 | 21.0 | 87.9 | 5.0 | 6.7 |
| Grower 0, .50 | 21.7 | 88.3 | 5.1 | 7.1 |
| Grower 50, 0 | 20.0 | 88.0 | 5.1 | 7.3 |
| Grower 50, .25 | 21.8 | 87.3 | 4.9 | 6.8 |
| Grower 50, .5 | 21.8 | 87.4 | 4.8 | 6.5 |

Birds were group weighed by pen on days one, fourteen and twenty-eight. Starter and grower feed consumption was also measured by pen. All birds which died during the trial were weighed and this weight was used to determine an adjusted feed conversion rate.

Birds were reared in start to finish battery units. Each experimental unit was equipped with a stainless steel feed trough and a plastic water cup. Bird comfort was maintained throughout the trial utilizing a thermostatically controlled forced air heater and exhaust fan. Initial room temperature was 88° F.

Results were analyzed using the General Linear Means procedure of SAS. Pen means served as the experimental unit in all analysis. Treatment means were generated using the LSMeans procedure and all significant means (Pr<0.05) were separated using the repeated t-test. Mortality data was transformed using the square root transformation to normalize data distribution.

Results:

Average weights, feed conversion, fed consumption and mortality for day 14 and 28 are shown in Table 3. No differences were found in initial group weights and therefore this information was omitted. No significant interactions were observed for the BMD-50× strain 2084 factorial. Therefore results are summarized by diet and by the main effects of BMD-50 and strain 2084. The fourteen day feed-to-gain ratio was significantly influenced by strain 2084 with the best results occurring for the 0.25% inclusion rate. Fourteen day average body weight, feed consumption and mortality were not significantly influenced by BMD-50 or strain 2084. Both twenty-eight day feed-to-gain and feed consumption were significantly impacted by the inclusion of strain 2084 with the 0.50% inclusion rate supporting a significantly better feed-to-gain rate as compared to diets which contained 0% or 0.25% strain 2084. Results support the conclusion that the strain 2084 does improve the feed conversion of male broiler chicks regardless of the inclusion of dietary BMD-50. The diets used in this trial contained a generous level of nutrients (105% of NRC recommendation) and it may be beneficial to test the effects of dietary strain 2084 on broilers receiving diets with a smaller safety margin of excess nutrients.

TABLE 3

Results of feeding *Bacillus* strain 2084 to Male Broiler Chickens Grown to 28 days of age

| BMD (g/ton) | 2084 (%) | Day 14 | | | | Day 28 | | | |
|---|---|---|---|---|---|---|---|---|---|
| | | Average Weight (g) | Feed-to-Gain (g:g) | Feed Consumed (g) | Mortality (%) | Average Weight (g) | Feed-to-Gain (g:g) | Feed Consumed (g) | Mortality (%) |
| 0 | 0 | 379 | 1.266 | 484 | 0 | 1235 (17) | 1.510$_{ab}$ | 1883$_a$ (29) | 3.33 |
| 0 | 0.25 | 391 | 1.235 | 481 | 3.7 | 1206 (17) | 1.470$_a$ | 1817$_{abc}$ (30) | 3.7 |
| 0 | 0.5 | 378 | 1.296 | 492 | 0 | 1231 (16) | 1.434$_d$ | 1737$_c$ (38) | 7.57 |
| 50 | 0 | 398 | 1.253 | 495 | 1.67 | 1216 (16) | 1.520$_a$ | 1848$_{ab}$ (29) | 1.67 |
| 50 | 0.25 | 391 | 1.233 | 482 | 0 | 1228 (19) | 1.489$_{bc}$ | 1825$_{abc}$ (35) | 2.08 |
| 50 | 0.5 | 385 | 1.283 | 494 | 0 | 1229 (17) | 1.460$_{cd}$ | 1771$_{bc}$ (35) | 1.67 |
| SEM | | 8 | 0.02 | 8 | 1 | | 0.01 | | 2 |
| Pr > F | | 0.4159 | 0.2017 | 0.6911 | 0.1754 | 0.8398 | 0.0001 | 0.048 | 0.3384 |
| 0 | | 382 | 1.266 | 486 | 1.18 | 1225 | 1.472 | 1815 | 4.94 |
| 50 | | 391 | 1.256 | 491 | 0.67 | 1224 | 1.489 | 1812 | 1.75 |
| SEM | | 4.6 | 0.011 | 4 | 0.7 | 10 | 0.006 | 18 | 1.2 |
| Pr > F | | 0.1477 | 0.5559 | 0.4706 | 0.6066 | 0.9375 | 0.0674 | 0.9147 | 0.0766 |
| | 0 | 388 | 1.260$_{ab}$ | 489 | 0.833 | 1226 | 1.515$_a$ | 1865$_a$ (20) | 2.5 |
| | 0.25 | 391 | 1.234$_b$ | 482 | 1.94 | 1217 | 1.480$_b$ | 1820$_{ab}$ (22) | 2.85 |
| | 0.5 | 381 | 1.289$_a$ | 493 | 0 | 1231 | 1.448$_c$ | 1755$_b$ (25) | 4.68 |
| | SEM | 5 | 0.014 | 5 | 0.9 | 12 | 0.008 | | 1 |
| | Pr > F | 0.4591 | 0.0302 | 0.3532 | 0.3006 | 0.7114 | 0.0001 | 0.0065 | 0.541 |

Example 3

Bacillus subtilis Strain 2084 Broiler Pen Research Trial

Introduction:

In a trial conducted previously with male broiler chicks reared in battery cages to 28 d, supplementation with strain 2084 resulted in improved feed conversion compared to birds not provided strain 2084, and compared to those provided antibiotic (BMD) supplementation. The current study was conducted to further evaluate the effects of strain 2084 on the performance of broilers to market age.

Materials and Methods: A total of 500 male broiler chicks (Ross×Cobb 500) were divided into 10 pens and fed one of two dietary treatments (5 pens/treatment) in a completely randomized design in a 48 d study. Dietary treatments included: a control—typical commercial diet and a treatment—control diet supplemented with strain 2084 at an inclusion rate of $7.5 \times 10^4$ CFU/g.

Diets were fed in four phases: a starter diet from d 0 to 14, a finisher diet from d 15 to 32, a withdrawal diet from d 33 to 43, and a final withdrawal diet from d 44 to 48. All diets were pelleted at 85° C. (185° F.), and the starter diet was crumbled. Dietary treatments were administered throughout each phase of the trial.

Pen weights were obtained on d 0, 14, 32, 42, and 48 of the trial, and the total number of birds within each pen was used to determine an average body weight for individual birds. Feed consumption for each pen was determined from d 0 to 14, d 15 to 32, d 33 to 42, d 43 to 48. Birds were checked for mortality twice daily, and dead weights were used to correct for feed utilization for each pen.

Birds were maintained in an environmentally controlled room containing pens with concrete flooring and kiln pine shavings for litter. Room temperature was maintained at 31° C. (88° F.) using thermostatically controlled heaters.

Results:

Supplementation with strain 2084 did not affect body weight, feed intake, or feed conversion of broilers at the 14 and 32 d time periods compared to control birds (Tables 4 and 5). However, broilers provided Bacillus subtilis Strain 2084 had greater (P=0.056) body weight than birds fed the control diet at d 43 of the trial (Table 6), and improved feed/gain compared to control birds at d 48 (Table 7).

TABLE 4

Evaluation of broiler chickens fed a program with Bacillus subtilis 2084 on d 14 of the experiment.

| Treatment | Weight (g) | Feed/Gain[1] | Feed Intake (g) | Mortality % |
|---|---|---|---|---|
| Control | 385 | 1.127 | 437 | 2.40 |
| Bacillus 2084 | 378 | 1.183 | 451 | 1.25 |
| P Value | 0.37 | 0.33 | 0.46 | 0.64 |

TABLE 5

Evaluation of broiler chickens fed a program with Bacillus subtilis 2084 on d 32 of the experiment.

| Treatment | Weight (g) | Feed/Gain[1] | Feed Intake (g) | Mortality % |
|---|---|---|---|---|
| Control | 1604 | 1.434 | 2326 | 5.77 |
| Bacillus 2084 | 1607 | 1.417 | 2303 | 3.99 |
| P Value | 0.87 | 0.49 | 0.43 | 0.41 |

TABLE 6

Evaluation of broiler chickens fed a program with Bacillus subtilis 2084 on d 43 of the experiment.

| Treatment | Weight (g) | Feed/Gain[1] | Feed Intake (g) | Mortality % |
|---|---|---|---|---|
| Control | 2371 | 1.798 | 4430 | 8.87 |
| Bacillus 2084 | 2413 | 1.753 | 4355 | 6.99 |
| P Value | 0.059 | 0.14 | 0.23 | 0.57 |

TABLE 7

Evaluation of broiler chickens fed a program with Bacillus subtilis 2084 on d 48 of the experiment.

| Treatment | Weight (g) | Feed/Gain[1] | Feed Intake (g) | Mortality % |
|---|---|---|---|---|
| Control | 2675 | 1.956 | 6045 | 16.00 |
| Bacillus 2084 | 2732 | 1.921 | 5594 | 10.52 |
| P Value | 0.77 | 0.024 | 0.34 | .0.31 |

[1]Adjusted feed/gain; meaning the weight of all mortality was included in the adjusted feed/gain calculation.

High environmental temperatures and humidity during the last 10 days of the experiment resulted in higher mortality due to heat stress at the d 43 and d 48 time points (Table 6 and 7). Although not statistically significant, mortality was numerically decreased with strain 2084 supplementation at each time point during the trial, with final mortality decreasing by 34% in strain 2084-supplemented broilers compared to control birds (Tables 4-7).

Conclusion: Strain 2084 supplementation improved feed/gain in broilers evaluated to market age, and confirmed the improvement in feed conversion observed with strain 2084 supplementation in a previous study. Additionally, strain 2084 supplementation increased body weight of broilers in the current experiment, and may have provide a health benefit as indicated by numerically lower mortality rates compared to control birds.

Example 4

The Effect of a Bacillus subtilis Feed Additive on Improvement of Turkey Performance Introduction Maintaining optimum gut health is a critical step in the production of commercial turkeys. Poor gut health and enteritis caused by pathogens such as E. coli and Clostridium perfringens often the result of reduced nutrient absorption. Additionally, managing feed costs is essential to the overall profitability of turkeys. This evaluation demonstrated the ability of a Bacillus based direct-fed microbial (DFM) to improve livability and body weight of commercial turkeys. The Bacillus DFM consisted of three strains of Bacillus subtilis selected for their ability to control pathogenic E. coli and clostridia.

Scope of Investigation

Production data was collected. Trial 1, below, consisted of 84 barns of non-treated control turkey hens and 70 houses of hen turkeys fed the Bacillus DFM.

Trial 1 Effect of *Bacillus* DFM feed additive on performance of Turkeys.

| Performance Variable | Treatments | |
|---|---|---|
| | Control | *Bacillus* DFM |
| Number hens finished | 905,725 | 741,145 |
| Livability (%) | 94.16 | 94.66 |
| Body Weight (lb.) | 16.61 | 16.85 |
| Wt. adjusted Feed Conversion | 2.00 | 2.01 |
| Days to Market | 95.7 | 95.8 |

Trial 2, below, consisted of 140 barns of non-treated control turkey hens and 105 houses of hen turkeys fed the *Bacillus* DFM. During both trials the hen turkeys fed the *Bacillus* DFM did not get the regular growth promotion antibiotic. The *Bacillus* feed additive contained strains 2084, 15AP4 and LSSAO1 (added at equal amounts) fed at a rate of $7.5 \times 10^4$ CFU/g of feed. The *Bacillus* DFM was added at the rate of one pound per ton of feed from start to finish.

Results are presented.

Trial 2 Effect of *Bacillus* DFM feed additive on performance of Turkeys.

| Performance Variable | Treatments, | |
|---|---|---|
| | Control | *Bacillus* DFM |
| Number hens finished | 1,489.285 | 1,130,258 |
| Livability (%) | 94.35 | 94.80 |
| Body Weight (lb.) | 15.90 | 16.00 |
| Wt. adjusted Feed Conversion | 2.06 | 2.06 |
| Days to Market | 92.1 | 92.3 |

Conclusion:

This study demonstrated the ability of *Bacillus* DFM to improve growth and performance. In trial 1, the improved livability, body weight and medication cost resulted in 1:3.8 return on investment (ROI). In trial 2, the improved livability, body weight and condemnation resulted in 1:2.7 ROI.

Example 5

Effect of *Bacillus* CSI on Layer Production

*Bacillus* CSI Formulation Development:

Gastrointestinal tracts (GIT) were collected from numerous barns across three production sites. The GIT samples were plated and *E. coli* isolates were obtained. *E. coli* isolates were then tested using a multiplex PCR, those that contained two or more of the targeted genes were determined to be pathogenic and selected for further analysis. Eight hundred and thirty-five *E. coli* isolates were deemed to be avian pathogenic and were ran analyzed with RAPD PCR. The resulting fingerprint from each strain was then compiled into a dendrogram and clusters based on similarity were formed. Isolated that represent each cluster was tested to determine inhibition by *Bacillus* strains. Three *Bacillus* strains were found that were able to inhibit 96% of the total population of APEC isolates represented in the dendrogram. The average inhibition of these strains was 64%. The three strains 2084, LSSAO1, and BS27 were therefore chosen for the *Bacillus* CSI formula at an inclusion rate of $7.5 \times 10^4$ CFU/g. The strains were added at equal amounts in this and all examples using a combination of strains. This combination was then tested in a feeding trial situation.

*Bacillus* CSI Trials:

Two individual CSI trials were completed. Objectives of these trials were to establish performance reference points and determine the impact of *Bacillus* CSI in order to quantify benefits of the *Bacillus* CSI program while also monitoring the bacterial APEC challenges.

Trial 1:

Trial 1 was a trial that consisted of 9 control flocks that did not receive any *Bacillus* CSI product and 10 *Bacillus* CSI product treated flocks. Bovan and W36 breeds were used for this feeding trial. Flocks included in this trial ranged in age from 16 wks to 72 wks at the start. Paired control and treated flocks that were similar in age and breed were paired. Table 8, below, provides information regarding the flocks used within this trial. Shown are the complex, age, and breed of each flock along with its paired control.

TABLE 8

Flock information for Trial 1

| Treated Flocks | | | Age | Paired Control Flocks | | |
|---|---|---|---|---|---|---|
| Complex | House | Breed | (weeks) | Complex | House | Breed |
| BL | 10 | W36 | 72 | BL | 15 | W36 |
| BL | 11 | Bovan | 54 | BL | 14 | Bovan |
| BL | 32 | Bovan | 25 | BL | 29 | Bovan |
| BL | 31 | W36 | 17 | BL | 30 | W36 |
| BL | 18 | W36 | 16 | BL | 19 | W36 |
| BR | 17 | Bovan | 60 | BR | 19 | Bovan |
| BR | 2 | Bovan | 35 | BR | 32 | Bovan |
| BR | 22 | Bovan | 31 | BR | 21 | Bovan |
| HP | 54 | Bovan | 16 | No pair | | |
| HP | 61 | W36 | 16 | HP | 57 | W36 |
| HP | 58 | Bovan | 16 | HP | 60 | Bovan |

Treated birds were fed the *Bacillus* CSI product for 10 consecutive weeks. During the 10 weeks of feeding production data was gathered, and gastrointestinal tract samples (GIT) were collected at week 2, 4, 6, 8, and 10 of the feeding period from five of the treated flocks and 4 of their paired control flocks in order to assess microbiological differences. Production data continued to be gathered after the withdrawal of the *Bacillus* CSI product for the remaining life of the flock in order to assess any carry over value of use. Historical production data was also collected for Michael Foods in order to make appropriate comparisons.

Trial 2:

Trial 2 consisted of 8 control flocks that did not receive any *Bacillus* CSI product and 4 *Bacillus* CSI product treated flocks. Bovan and W36 breeds were used for this feeding trial. Flocks included in this trial ranged in age from 13 wks to 15 wks of age at the start. Control and treated flocks were again paired based on age and breed. Table 9, below, provides information regarding the flocks used within this trial. Shown are the complex, age, and breed of each flock along with its paired control.

TABLE 9

Flock information for Trial 2

| Complex | House | Breed | Age (weeks) | Complex | House | Breed |
|---|---|---|---|---|---|---|
| HP | 2 | W36 | 15 | HP | 15 | W36 |
| BL | 4 | W36 | 13 | BL | 12 | W36 |

TABLE 9-continued

Flock information for Trial 2

| Complex | House | Breed | Age (weeks) | Complex | House | Breed |
|---|---|---|---|---|---|---|
| HP | 17 | Bovan | 14 | HP | 6 | Bovan |
| BL | 15 | W36 | 13 | BL | 10 | W36 |

Treated birds were fed the *Bacillus* CSI product for 10 consecutive weeks. During the 10 weeks of feeding production data was gathered, and gastrointestinal tract samples (GIT) were collected at week 2, 4, 6, 8, and 10 of the feeding period from the four treated flocks and the four control flocks in order to assess microbiological differences. Historical production data continued to be collected for Michael Foods in order to make appropriate comparisons.

Production results were combined for both feeding trials. Production components of evaluation were: the monitoring of *E. coli* populations from the gastrointestinal tracts (GIT), benchmarking MFI historical performance, and the economic modeling of *Bacillus* CSI product impact. Performance reference points included were paired flocks of similar age and breed within the same complex. The period of evaluation was 10 weeks of dosing plus any carry over effect. Benchmarking was done against relative life of the flock performance for MFI average, paired flocks and control flocks. The life of flock impact was based on MFI average performance, which was required to accurately assess the value of reduced early mortality.

Figure 4:
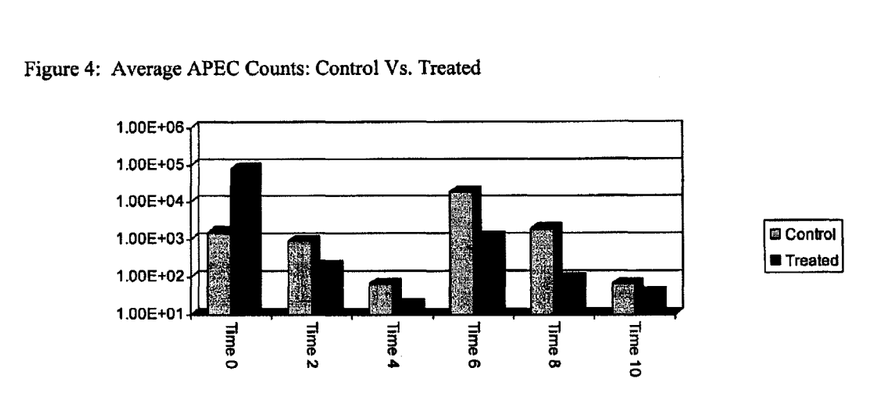
FIG. 4 is a graph showing the average Avian Pathogenic *E. coli* (APEC) Counts in control birds versus treated birds and demonstrates the reduction of bacterial APEC in gastrointestinal tract samples over a 10-week *Bacillus* CSI product feeding period in trial #1 of Example 5.

Results:
Microbiological:

FIG. 4 demonstrates the reduction of bacterial Avian Pathogenic *E. coli* in the GIT samples over the 10 week *Bacillus* CSI product feeding period in trial #1.

Figure 5:
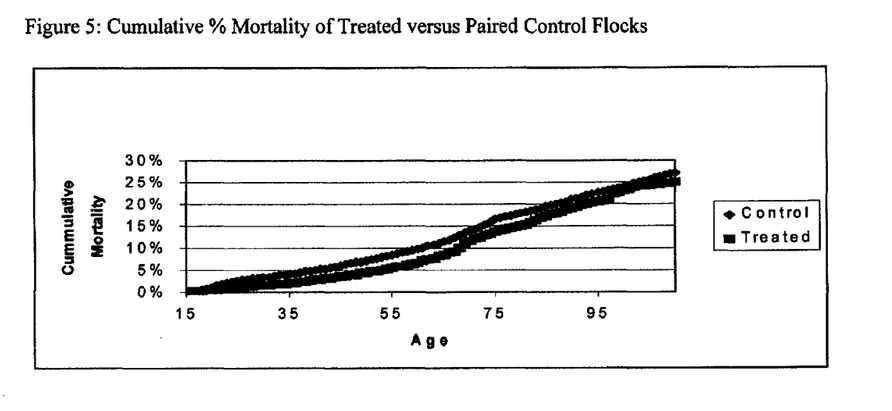
FIG. 5 is a graph showing cumulative percent mortality of treated versus paired control flocks of Example 5 and represents the cumulative percent mortality of a composite of all the control flocks compared to all treated flocks. Each tick mark on the graph would represent a week.

FIG. 5 represents the cumulative percent mortality of a composite of all the control flocks compared to all treated flocks. Each tick mark on the graph would represent a week.

The gross revenue generated by the use of the *Bacillus* CSI product due to the reduction in early mortality due to bacterial avian pathogenic *E. coli* is shown in Table 10.

TABLE 10

Revenue Generated: Treated versus Control Flocks

| Variable | MFI/Control Flocks | MFI: CSI Treated Flocks |
|---|---|---|
| Hens Housed | 140,000 | 140,000 |
| Feed Cost (wk. 17-110) | 852,144 | 858,703 (increases cost due cost of CSI product) |
| Pullet Cost | 371,000 | 371,000 |
| Egg Revenue through 110 wks. (Based on $/Dozen) | 2,513,974 | 2,543,154 |
| Egg Revenue through 110 wks. (Based on $/lb.) | 2,66,,560 | 2,685,791 |
| Gross Margin (Dozen) | 1,290,831 | 1,313,451 |
| Gross Margin (lbs.) | 1,438,417 | 1,456,088 |
| Benefit of using CSI/dozen of eggs | | $22,620 generated above the control flocks |
| Benefit of using CSI/lb of eggs | | $17,671 generated above the control flocks |

Summary:

The *Bacillus* based product was successful at reducing bacterial APEC levels in the gastrointestinal tract when directly compared to similar control flocks. This reduction in pathogenic organisms led to reduced mortality and morbidity in the treated flocks. This reduction directly led to a $22,620 profit per treated flock based on dozen per eggs produced and a $17,671 profit per treated flock based on lbs. per egg produced Example 6

The Effect of a *Bacillus* CSI Feed Additive on Reducing Necrotic Enteritis and Improving Performance of Broilers Introduction Maintaining optimum gut health is critical. Poor gut health and enteritis, caused by pathogens such as *Clostridium perfringens*, are often the result of reduced nutrient absorption. Additionally, managing feed costs is essential to the overall profitability of poultry. This evaluation demonstrated the ability of *Bacillus* CSI product, a biological feed additive, to lower the incidence of necrotic enteritis and improve production performance of broilers.

Scope of Investigation

Production data was collected from a farm with four houses. This farm had a history of necrotic enteritis and poor performance over the last 5 years. Two houses of 30,000 broilers were fed *Bacillus* CSI feed additive at one pound per ton, from start to market (62 days). The *Bacillus* feed additive contained strains 2084, 15A-P4 and LSSAO1 fed at a rate of $7.5 \times 10^4$ CFU/g of feed. Equal amounts of the strains were used. The other two houses of 30,000 broilers were fed a regular diet. Results are presented in Tables 11 and 12.

TABLE 11

Effect of the *Bacillus* CSI on performance of broilers.

| | Treatment | |
|---|---|---|
| Performance Variable | Control | *Bacillus* CSI |
| Livability (%) | 85.55 | 89.70 |
| Body Weight (lb.) | 8.25 | 8.14 |
| Feed Conversion (after condemnation (%)) | 2.28 | 2.24 |
| Total Condemnation (DOA, WB and parts (%)) | 2.40 | 1.88 |
| Days to Market | 62 | 62 |

TABLE 12

The Economic Advantage.

| Performance Variable | *Bacillus* CSI Advantage | Financial Advantage $$ |
|---|---|---|
| Livability (%) | 4.2 | $3,830 |
| Feed Conversion | 4 points | $772 |
| Condemnation | 0.6 | $555 |
| Total Advantage | | $5,157 |

Conclusion

This study demonstrated the ability of the *Bacillus* CSI product to control necrotic enteritis, improve livability, feed efficiency and condemnation of broilers. Birds fed the *Bacillus* CSI product did not break with clinical disease of Necrotic Enteritis. The observed benefits of *Bacillus* CSI resulted in a per bird improvement of $0.1770 over the non treated birds.

Example 7

Introduction

The incidence of cellulitis in turkeys has been increasing in the last three years causing significant financial loss to the turkey industry. It is a disease that affects mature turkeys close to market age with quick onset and sudden mortality. It is caused by *Clostridium perfringens* and *Clostridium septicum*. This evaluation demonstrated the ability of a *Bacillus* CSI feed additive to reduce the incidence of cellulitis and improve livability and performance.

Scope of Investigation

Production data was collected from 10 barns of treated turkey toms and 40 houses of non-treated turkey toms. During the trial the CSI fed turkeys did not get the regular growth promotion antibiotic. The *Bacillus subtilis* based CSI feed additive contained strains 2084, LSSAO1 and 15A-P4 in equal amounts and was added at the rate of one pound per ton of feed from start to finish to supply the *Bacillus* at a rate of $4.75 \times 10^4$ CFU/g of final feed. The results are presented below in Tables 13 and 14.

TABLE 13

Effect of the *Bacillus* CSI feed additive on performance of Turkeys.

|  | Treatments | |
| --- | --- | --- |
| Performance Variable | Control | *Bacillus* CSI |
| Number toms finished | 240,000 | 60,000 |
| Livability (%) | 86.23 | 87.04 |
| Condemnation (%.) | 2.20 | 1.81 |
| Wt. adjusted Feed Conversion | 2.66 | 2.64 |

TABLE 14

Effect of the *Bacillus* CSI feed additive on performance of Turkeys.

|  | Treatments, | |
| --- | --- | --- |
| Performance Variable | Previous 3 flock average | *Bacillus* CSI treated flocks |
| Number hens finished | 180.000 | 60,000 |
| Livability (%) | 84.86 | 87.04 |
| Condemnation (%) | 2.51 | 1.81 |
| Wt. adjusted Feed Conversion | 2.66 | 2.64 |

Conclusion:

This study demonstrated the ability of CSI feed additive to reduce the incidence of cellulitis and replace conventional growth promotion antibiotics in the feed with equal or improved performance.

Example 8

Development of a *Bacillus* CSI Direct-Fed Microbial and Application for Litter *Salmonella* Reduction in Broilers

Introduction

The use of a direct-fed microbial product can stimulate a host's microflora and, indirectly, its environment. A reduction in gram-negative bacterial challenges in a host's environment can help improve performance. In the poultry industry, *Salmonella* is a serious environmental and food safety challenge. The objective of this study is to determine if a *Bacillus* CSI product can impact the *Salmonella* levels in the litter of broilers.

*Bacillus* CSI Product Development

The *Bacillus* CSI product \was based on the *E. coli* and *Clostridium perfringens* that were previously collected at five farms. A total of 1115 *E. coli* were collected of which, 441 contained two or more virulence genes and, therefore, were considered to be avian pathogenic *E. coli* (APEC). A total of 232 *Clostridium* was also collected and 154 typed out as *Clostridium perfringens* type A. The pathogenic *E. coli* and *Clostridium* were used in a bacteriocin assay to develop a *Bacillus* feed product that would help control these pathogens. *Bacillus subtilis* strains LSSAO1, 2084 and 15A-P4 showed the best potential as a product against both the APEC and type A *Clostridium*, in vitro.

Feeding Trial

A total of five farms were tested (three from the West production system and two from the East production system) with four houses on each farm (two treated and two control). Classically good and poor performing farms were chosen for this study. The *Bacillus* CSI was added to a standard poultry diet at an inclusion rate of one pound per ton of finished feed. The product contained $1.5 \times 10^8$ CFU/g, giving a final count of $4.75 \times 10^4$ CFU/g of treated feed. The feeding trial was repeated immediately after the first phase was completed using the same farms on the West production system, but two different farms on the East production system.

*Salmonella* Drag Swab Analysis

The incidence of *Salmonella* in litter was determined by using a drag swab technique. All 20 houses were divided into three sections and sampled in duplicate for a total of six drag swabs per house. The swabs were added to mason jars with 90 ml sterile peptone water and shipped overnight to Agtech at ambient temperature. A 10 ml sample from each jar was enriched in 90 ml Tetrothianiate broth for 24 hours at 42° C. After incubation, the enrichment was struck onto Xylose-lysine-Tergitol 4 agar (XLT4) and Brilliant Green agar with novobiocin (BGAN) and incubated for 24 hours at 37° C. Typical *Salmonella* colonies appear black with a yellow halo on the XLT4 media and as a grayish colony on the BGAN agar. Suspect *Salmonella* colonies were incubated in selenite broth for 24 hours at 37° C. and tested for agglutination using the Wellcolex Colour *Salmonella* test to confirm and identify the colony as *Salmonella*.

*Salmonella* Drag Swab Results

Figure 6:
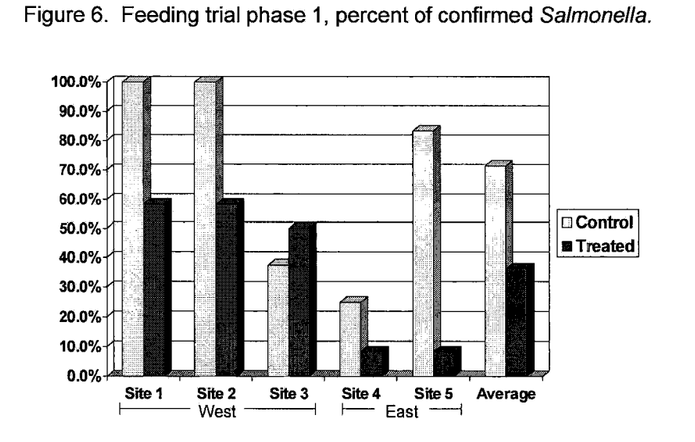
FIGS. 6 and 7 are graphs showing the percent of confirmed *Salmonella* at various sites described in Example 9 from phase 1 (FIG. 6) and phase 2 (FIG. 7) of a feeding trail. A total of 120 drag swabs were taken for each phase of the feeding trial.
Figure 7:
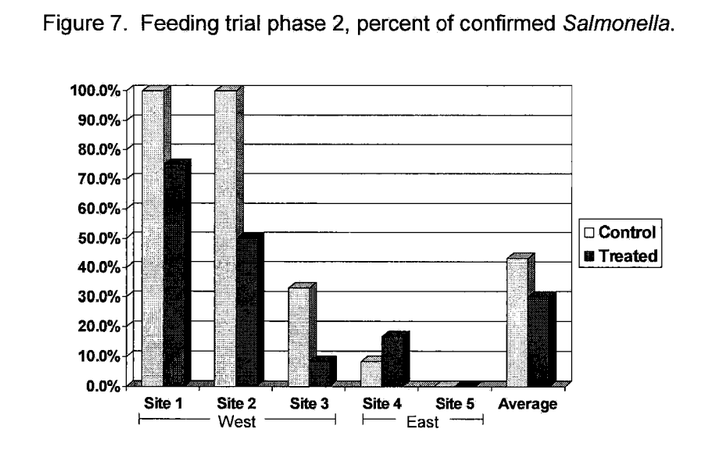

A total of 120 drag swabs were taken for each phase of the feeding trial. FIGS. 6 and 7 show the percent of confirmed *Salmonella* at each site.

Summary

The *Bacillus*. CSI product was developed using the *E. coli* and *Clostridium* that were previously collected at five farms. This product was implemented into a two phase feeding trial and *Salmonella* drag swabs were collected to determine if the product could reduce *Salmonella* load in the litter.

In phase 1, sites 1, 2' and 5 showed a dramatic reduction in percent *Salmonella* in the treated houses compared to the control houses. In phase 2, sites 1 and 2 continued to show a reduction in percent of *Salmonella* in the treated houses compared to the control houses. The average *Salmonella* in phase 1 was 34.8% lower in the treated houses compared to the control houses. The average *Salmonella* in phase 2 was 13.3% lower in the treated houses compared to the control houses. While the average *Salmonella* challenge was not as high in phase 2, the treated houses continued to show a reduction in *Salmonella*.

With the continued use of this *Bacillus* CSI product, pathogen levels will continue to be reduced, allowing the birds an opportunity to improve its overall gut microbial population. This in turn can improve the bird's performance and environment and is an important food safety measure.

Example 9

**Development of a *Bacillus* CSI Direct-Fed Microbial and Application for Improving Turkey Performance**

CSI Development

The *Bacillus* CSI formulation was developed based on the *E. coli* and *Clostridium* collected from the gastrointestinal tract of turkeys at several of their farms. A total of 510 *E. coli* were collected during three separate necropsy sessions of which, 194 contained two or more virulence genes and, therefore, are considered to be avian pathogenic *E. coli* (APEC). A total of 92 *Clostridium* was also collected and 23 typed out as *Clostridium perfringens* type A. The pathogenic *E. coli* and *Clostridium* were used in a bacteriocin assay to develop a CSI product that would help control these pathogens. *Bacillus subtilis* strains LSSAO1, 2084 and 15A-P4 showed the best potential as a product against both the APEC and type A *Clostridium*, in vitro. The strains were used in equal amounts at an inclusion rate of $7.5 \times 10^4$ CFU/g.

Feeding Trial

The *Bacillus* CSI product was added to the feed. Feed mill A manufactured diets 1 and 2 for all turkeys; therefore, all turkeys initially received the *Bacillus* CSI. Feed mill B made diets 3 through market for a portion of the birds while feed mill A produced *Bacillus* CSI treated feed for the remainder of the turkeys. The turkeys fed from feed mill A throughout the trial were considered true *Bacillus* CSI treated turkeys. The turkeys fed from feed mill B that initially received *Bacillus* CSI for diets 1 and 2 only were the control turkeys. *Bacillus* CSI was added to a standard turkey diet at an inclusion rate of one pound per ton of finished feed. The *Bacillus* CSI product contained $1.5 \times 10^8$ CFU/g, giving a final count of $4.75 \times 10^4$ CFU/g of treated feed.

Performance Results

A total of ten flocks received the full *Bacillus* CSI treatment and seven flocks, which are considered control, received *Bacillus* CSI in diets 1 and 2 only, and then received Stafac or BMD in the remaining diets. Table 15 shows the performance data for the average of the treated and control flocks.

TABLE 15

Performance summary of average treated and control flocks.

| | Treated | Control |
|---|---|---|
| 14 day mortality (%) | 4.06 | 3.99 |
| Age (days) | 130.4 | 131.3 |
| Gross weight (LB) | 36.48 | 35.90 |
| Average weight (LB)* | 36.82 | 35.90 |
| Average Daily Gain (LB/day) | 0.2797 | 0.2733 |
| Adjusted Feed Conversion (LB:LB) | 2.5581 | 2.5725 |
| Gross Livability (%) | 82.85 | 82.93 |
| Net Livability (%) | 82.22 | 82.53 |
| Total Condemnation (%) | 1.92 | 1.78 |

*Adjusted weight to 131.3 days

Microbiological Results

The gastrointestinal tract of both treated and control birds were analyzed at 9 and 18 weeks of age to enumerate for *E. coli* and *Clostridium*. FIG. 6 shows the total *E. coli* count and the confirmed APEC count for the treated and control birds at 9 and 18 weeks of age. At 9 weeks of age the control and treated birds had similar *E. coli* counts and confirmed APEC counts. The percent of APEC in the control birds was 21.7% and 42.0% in the treated birds. At 18 weeks of age the *E. coli* counts and confirmed APEC counts were three logs lower in the treated birds compared to control birds. The percent of APEC in the control birds was 55.3% and 38.7% in the treated birds.

FIG. 7 shows the total *Clostridium* and confirmed *Clostridium perfringens* type A count for the treated and control birds at 9 and 18 weeks of age. At 9 weeks of age the control and treated birds had similar *Clostridium* counts and confirmed *C. perfringens* type A counts. The percent of *C. perfringens* type A in the control birds was 66.0% and 27.5% in the treated birds. At 18 weeks of age the *Clostridium* counts and confirmed *C. perfringens* type A counts were three logs lower in the treated birds compared to control birds. The percent of *C. perfringens* type A in the control birds was 90.9% and 83.6% in the treated birds.

Summary

The comparison between treated and control flocks shows that the *Bacillus* CSI product improved feed conversion by 2 pts and 0.92 lbs. This improvement may be due to a three log reduction in APEC and *Clostridium perfringens* type A at 18 weeks of age. *Bacillus* CSI fed the entire production phase has provided a biological tool that can improve performance by controlling and maintaining microbial gut populations.

The invention is not intended to be limited to the preferred embodiments described above. Thus, the invention encompasses all alternate embodiments that fall literally or equivalently within the scope of these claims.

What is claimed is:

1. An isolated *Bacillus subtilis* strain having all the identifying characteristics of the *Bacillus* strain LSSAO1 Accession No. NRRL B-50104.

2. A method comprising administering to one or more birds an effective amount of one or more isolated *Bacillus* strains chosen from strains BS27 Accession No. NRRL B-50105, 2084 Accession No. NRRL B-50013, and LSSAO1 Accession No. NRRL B-50104, alone or in combination with, an effective amount of at least one or more isolated *Bacillus* strains chosen from strains 3A-P4 ATCC Accession No. PTA-6506, 15A-P4 ATCC Accession No. PTA-6507, 22C-P1 ATCC Accession No. PTA-6508, wherein the administration of the strain provides at least one benefit chosen from increasing low G+C, gram positive bacteria in the gastrointestinal flora of the bird and inhibiting a pathogen chosen from at least one of *E. coli*, *Salmonella*, and *Clostridium* in the one or more birds.

3. The method of claim 2, wherein the *Bacillus* strain is 2084 Accession No. NRRL B-50013.

4. The method of claim 2, wherein *Bacillus* strains 22C-P1 ATCC Accession No. PTA-6508, 2084 Accession No. NRRL B-50013, and BS27 Accession No. NRRL B-50105 are administered.

5. The method of claim 2, wherein *Bacillus* strains LSSAO1 Accession No. NRRL B-50104 and 3A-P4 ATCC Accession No. PTA-6506 are administered.

6. The method of claim 2, wherein *Bacillus* strains LSSAO1 Accession No. NRRL B-50104 and 2084 Accession No. NRRL B-50013 are administered.

7. The method of claim 2, wherein from $7.5 \times 10^3$ CFU of the *Bacillus* strain per gram of feed to $7.5 \times 10^5$ CFU of the *Bacillus* strain per gram of feed is administered.

8. The method of claim 7, wherein about $7.5 \times 10^4$ CFU of the *Bacillus* strain per gram of feed is administered.

9. The method of claim 2, wherein the bird is a turkey.

10. The method of claim 9, wherein the turkey is a finishing turkey.

11. The method of claim 10, wherein *Bacillus* strains 22C-P1 ATCC Accession No. PTA-6508, 2084 Accession No. NRRL B-50013, and BS27 Accession No. NRRL B-50105 are administered.

12. The method of claim 10, wherein the administering step alters the gastrointestinal flora of the finishing turkey similar to alteration provided by the growth promoting antibiotic virginiamycin.

13. The method of claim 9, wherein *Bacillus* strains 15A-P4 ATCC Accession No. PTA-6507, 2084 Accession No. NRRL B-50013, and LSSAO1 Accession No. NRRL B-50104 are administered.

14. The method of claim 13, wherein the administering step reduces levels of *C. perfringens* type A in the turkey.

15. The method of claim 2, wherein the bird is a broiler.

16. The method of claim 15, wherein *Bacillus* strains 15A-P4 ATCC Accession No. PTA-6507, 2084 Accession No. NRRL B-50013, and LSSAO1 Accession No. NRRL B-50104 are administered.

17. The method of claim 16, wherein the administering step reduces the level of *Salmonella* present in the litter of the broiler.

18. The method of claim 2, wherein the bird is a layer.

19. The method of claim 18, wherein *Bacillus* strains 2084 Accession No. NRRL B-50013, LSSAO1 Accession No. NRRL B-50104, and BS27 Accession No. NRRL B-50105 are administered.

20. The method of claim 19, wherein the administering step reduces the level of avian pathogenic *E. coli* in the layer.

21. The method of claim 20, wherein the reduced level of avian pathogenic *E. coli* in the layer reduces mortality and morbidity in the layer.

* * * * *

SEQUENCE LISTING

<160> NUMBER OF SEQ ID NOS: 10

<210> SEQ ID NO 1
<211> LENGTH: 57
<212> TYPE: DNA
<213> ORGANISM: Artificial Sequence
<220> FEATURE:
<223> OTHER INFORMATION: Synthetic DNA - primer

<400> SEQUENCE: 1
cgcccgccgc gccccgcgcc cgtcccgccg ccccgcccg aacgcgaaga accttac       57

<210> SEQ ID NO 2

```
<211> LENGTH: 17
<212> TYPE: DNA
<213> ORGANISM: Artificial Sequence
<220> FEATURE:
<223> OTHER INFORMATION: Synthetic DNA - primer

<400> SEQUENCE: 2
cggtgtgtac aagaccc                                                        17

<210> SEQ ID NO 3
<211> LENGTH: 17
<212> TYPE: DNA
<213> ORGANISM: Artificial Sequence
<220> FEATURE:
<223> OTHER INFORMATION: Synthetic DNA - primer

<400> SEQUENCE: 3
aacgcgaaga accttac                                                        17

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA - primer

<400> SEQUENCE: 4
agagtttgat ymtggctcag                                                     20

<210> SEQ ID NO 5
<211> LENGTH: 15
<212> TYPE: DNA
<213> ORGANISM: Artificial Sequence
<220> FEATURE:
<223> OTHER INFORMATION: Synthetic DNA - primer

<400> SEQUENCE: 5
acgggcggtg tgtrc                                                          15

<210> SEQ ID NO 6
<211> LENGTH: 374
<212> TYPE: DNA
<213> ORGANISM: Unknown
<220> FEATURE:
<223> OTHER INFORMATION: BB28-7

<400> SEQUENCE: 6
tcgggaacat tggaagacag gtggtgcatg gttgtcgtca gctcgtgtcg tgagatgttg         60
ggttaagtcc cgcaacgagc gcaacccttα tcttcagtag ccagcaattc ggttgggcac        120
tctggagaga ctgccaggga gaacctggag gaaggtgggg atgacgtcaa atcatcatgc        180
cccttatggc cagggctaca cacgtgctac aatggcgtaa acaaagggaa gcgagcatgt        240
gagtgtgagc aaatctcaaa aataacgtct cagttcggat tgtagtctgc aactcgacta        300
catgaagctg gaatcgctag taatcgcgga tcagcatgcc gcggtgaata cgttcccggg        360
tcttgtacac accg                                                          374

<210> SEQ ID NO 7
<211> LENGTH: 361
<212> TYPE: DNA
<213> ORGANISM: Unknown
<220> FEATURE:
<223> OTHER INFORMATION: BB28-16
<220> FEATURE:
<221> NAME/KEY: misc_feature
<222> LOCATION: (93)..(93)
```

```
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t

<400> SEQUENCE: 7
agacaggtgg tgcatggttg tcgtcagctc gtgtcgtgag atgttgggtt aagtcccgca    60
acgagcgcaa cccttatctt cagtagccag cgnttcgggc gggcactctg agagactgc   120
cagggataac ctggaggaag gtggggatga cgtcaaatca tcatgcccct tatgggcagg   180
gctacacacg tgctacaatg gcgtaaacaa agggaggcan agccgcgagg ccgagcaaat   240
ctcaaaaata acgtctcagt tcggattgta gtctgcaact cgactacatg aagctggaat   300
cgctagtaat cgcgaatcag aatgtcgcgg tgaatacgtt cccgggtctt gtacacaccg   360
a                                                                   361

<210> SEQ ID NO 8
<211> LENGTH: 357
<212> TYPE: DNA
<213> ORGANISM: Unknown
<220> FEATURE:
<223> OTHER INFORMATION: BB28-6
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t

<400> SEQUENCE: 8
attgtttgca tggttgtcgt cagctcgtgt cgtgagatgt tgggttaagt cccgcaacga    60
gcgcaacccn tatctttagt agccagcatt taaggtgggc actctagaga gactgccagg   120
gataacttgg aggaaggtgg ggatgacgtc aaatcatcat gccccttatg accagggcta   180
cacacgtgct acaatggcgt aaacaaaggg aagcganacc gcgaggtgga gcaaatccca   240
aaaataacgt ctcagttcgg attgtagtct gcaactcgac tacatgaagc tggaatcgct   300
agtaatcgcg aatcagaatg tcgcggtgaa tacgttcccg ggtcttgtac acccga       357

<210> SEQ ID NO 9
<211> LENGTH: 416
<212> TYPE: DNA
<213> ORGANISM: Closterium sp.

<400> SEQUENCE: 9
acatccttct gactctcctt aatcggagat ttccttcggg gacagaagtg acaggtggtg    60
catggttgtc gtcagctcgt gtcgtgagat gttgggttaa gtcccgcaac gagcgcaacc   120
cttgccttta gttgccagca ttaagttggg cactctagag gactgccag gtaacctgg   180
aggaaggtgg ggatgacgtc aaatcatcat gccccttatg cttagggcta cacacgtgct   240
acaatgggtg gtacagaggg cagccaagtc gtgaggcgga gctaatccct taaagccatt   300
ctcagttcgg attgtaggct gaaactcgcc tacatgaagc tggagttact agtaatcgca   360
gatcagaatg ctgcggtgaa tgcgttcccg ggtcttgtac acaccgcccg tcacac       416

<210> SEQ ID NO 10
<211> LENGTH: 419
<212> TYPE: DNA
<213> ORGANISM: Closterium sp.
<220> FEATURE:
```

```
<221> NAME/KEY: misc_feature
<222> LOCATION: (173)..(173)
<223> OTHER INFORMATION: n is a, c, g, or t

<400> SEQUENCE: 10
acatcctttt gacctctccc taatcggaga tttcccttcg gggacagaag tgacaggtgg      60
tgcatggttg tcgtcagctc gtgtcgtgag atgttgggtt aagtcccgca acgagcgcaa     120
cccttgcctt tagttgccag cattaagttg ggcactctag agggactgcc agngataacc     180
tggaggaagg tggggatgac gtcaaatcat catgcccctt atgcttaggg ctacacacgt     240
gctacaatgg gtggtacaga gggcagccaa gtcgtgaggc ggagctaatc ccttaaagcc     300
attctcagtt cggattgtag gctgaaactc gcctacatga agctggagtt actagtaatc     360
gcagatcaga atgctgcggt gaatgcgttc ccgggtcttg tacacaccgc ccgtcacac     419
```